United States Patent [19]

Deubzer et al.

[11] 4,176,128
[45] Nov. 27, 1979

[54] PROCESS FOR INCREASING THE MOLECULAR WEIGHT OF SILICON COMPOUNDS

[75] Inventors: Bernward Deubzer, Burghausen; Norbert Egerter, Emmerting, both of Fed. Rep. of Germany

[73] Assignee: Wacker-Chemie GmbH, Munich, Fed. Rep. of Germany

[21] Appl. No.: 973,787

[22] Filed: Dec. 26, 1978

[30] Foreign Application Priority Data

Jan. 1, 1978 [DE] Fed. Rep. of Germany ....... 2801779

[51] Int. Cl.$^2$ ................................................ C07F 7/08
[52] U.S. Cl. ............................................. 260/448.2 E
[58] Field of Search ................................. 260/448.2 E

[56] References Cited

U.S. PATENT DOCUMENTS

| | | | |
|---|---|---|---|
| 3,489,782 | 1/1970 | Pruvost et al. | 260/448.2 E |
| 3,491,054 | 1/1970 | Thomas | 260/448.2 E X |
| 3,634,321 | 1/1972 | Nugent et al. | 260/448.2 E UX |
| 3,903,047 | 9/1975 | Ashby | 260/448.2 E X |
| 3,939,195 | 2/1976 | Lucking et al. | 260/448.2 E |

*Primary Examiner*—Paul F. Shaver

[57] ABSTRACT

The present invention relates to an improved process for increasing the molecular weight of silicon compounds and more particularly to an improved process for increasing the molecular weight of silicon compounds containing Si-bonded alkoxy groups.

2 Claims, No Drawings

PROCESS FOR INCREASING THE MOLECULAR WEIGHT OF SILICON COMPOUNDS

BACKGROUND OF INVENTION

A process for hydrolyzing a mixture of organoalkoxysiloxanes at an elevated temperature to form organopolysiloxanes is described in U.S. Pat. No. 3,634,321 to Nugent et al. Compared to the processes known heretofore, the process of this invention has the advantage that it provides a means for controlling the hydrolysis of the alkoxy groups and thus makes it easier to regulate the molecular weight of the resulting polysiloxane. Furthermore the process of this invention does not require a long heating period under reflux which was required in the prior processes. Therefore, the process of this invention does not require the energy which was required in the prior processes. Also, the process of this invention saves considerable time since the catalyst need not be neutralized before the product can be used. Finally, in the process of this invention the alcohol which is split off during the hydrolysis can be recovered more easily than has been possible heretofore.

Therefore, it is an object of this invention to provide an improved process for preparing organopolysiloxanes. Another object of this invention is to provide an improved process for increasing the molecular weight of silicon compounds. Still another object of this invention is to provide an improved process for controlling the molecular weight of organopolysiloxanes. A further object of this invention is to provide an improved process for preparing organopolysiloxanes without having to neutralize the catalyst.

SUMMARY OF INVENTION

The foregoing objects and others which will become apparent from the following description are accomplished in accordance with this invention, generally speaking, by providing a process for increasing the molecular weight of silicon compounds containing predominately Si-bonded alkoxy groups which comprises hydrolyzing the silicon compounds at an elevated temperature in the presence of hydrates of at least one salt selected from the group consisting of a salt of ammonium hydroxide and/or a metal of the first to the third principal group of the Periodic System of elements according to Mendeleeff in an amount of at least 8 grams of hydrated salt per mol of hydrolyzable group, while distilling off the alcohol as it is evolved to form a product which does not solidify when cooled to at least room temperature.

DETAIL DESCRIPTION OF INVENTION

Any silicon compound consisting predominately of Si-bonded alkoxy groups which could have been hydrolyzed heretofore may be used in the process of this invention. In other words, silicon compounds in which the Si-bonded alkoxy groups are predominately the only hydrolyzable groups, are those in which all or essentially all, i.e., at least 90 percent of the number of silicon valances which are not saturated by alkoxy groups, are saturated by atoms and/or groups which are inert under the prevailing reaction conditions. Examples of substitutents which are inert under the reaction conditions are siloxane oxygen atoms and/or hydrocarbon radicals. Silicon compounds containing Si-bonded alkoxy groups as the sole reactive group, are silanes represented by the general formula:

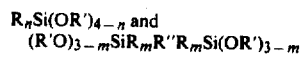

where R represents the same or different monovalent substituted or unsubstituted, hydrocarbon radicals; R' represents the same or different alkyl radicals having from 1 to 5 carbon atoms; R" represents the same or different bivalent hydrocarbon radicals; n is 0, 1, 2 or 3 and m is 0, 1 or 2; and siloxanes consisting of units of the general formula:

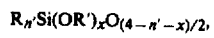

where R is the same as above; n' is 0, 1, 2 or 3 and on the average is from 0.0 to 2.1; x is 0, 1, 2 or 3 and on the average is from 0.01 to 3; and the sum of n'+x is on the average no greater than 3.99.

Examples of hydrocarbon radicals represented by R are alkyl radicals, such as the methyl, ethyl, n-propyl, isopropyl, n-butyl and the sec-butyl radical; as well as hexyl and octadecyl radicals; alkenyl radicals such as the vinyl and allyl radicals; cycloalkyl radicals such as the cyclohexyl radical; cycloalkenyl radicals such as the cyclohexenyl radical; aryl radicals such as the phenyl radical; aralkyl radicals such as o-, p- and m-tolyl radicals, and alkaryl radicals such as the benzyl radical.

Examples of substituted hydrocarbon radicals represented by R are especially haloalkyl radicals, such as the 3,3,3-trifluoropropyl radical; and the haloaryl radicals such as o-, m- and p-chlorophenyl radicals.

Because of their availability, it is preferred that at least 50 percent of the number of R radicals be methyl radicals. Other preferred R radicals which may be present are vinyl and/or phenyl radicals.

Other examples of alkyl radicals represented by R', in addition to those described above, are alkyl radicals having from 1 to 4 carbon atoms such as the tert-butyl radical as well as the pentyl radicals.

Examples of bivalent hydrocarbon radicals represented by R" are the ethylene and the phenylene radicals.

It is preferred that on the average n' not exceed about 1.8. Mixtures of various silicon compounds containing Si-bonded alkoxy groups which are substantially free of other reactive groups may be employed. However only one such type of silicon compound may be used.

It is preferred that the process of this invention be conducted at a temperature at which the alcohol which is split off under the pressure applied during the process, is distilled off from the reaction mixture. This temperature is preferably at least 30° C.

Examples of salt hydrates by which the water is introduced into the reaction vessel are the following: $Na_2CO_3.10H_2O$, $Na_2CO_3.7H_2O$, $Na_2SO_4.10H_2O$, $Ca(NO_3)_2.6H_2O$, $Al_2(SO_4)_3.18H_2O$, $Na_2HPO_4.12H_2O$, $NH_4Fe(SO_4)_2.12H_2O$ and $(NH_4)_2Fe(SO_4)_2.6H_2O$.

As can be seen from the above examples of salt hydrates, the cations present in these salts may be in addition to ammonium and/or cations of elements of the first to the third principal group of the Periodic System of the elements according to Mendeleeff, cations of other elements such as hydrogen and iron.

Sodium carbonate-decahydrate, i.e., a salt having the formula, $Na_2CO_3.10H_2O$ is the preferred hydrate because of its availability, its high water content and its low melting point which greatly facilitates its dispersion in the silicon compounds whose molecular weight is to be increased in accordance with the process of this invention. Moreover the dehydrated derivative has a high enough melting point that it recrystallizes subsequent to cooling, and can be easily removed by filtration.

The term "first through third principal group" as used herein, refers to Periods 2 through 6 of Groups I through III of the Periodic System of the elements which forms an appendix to "Lehrbuch der Anorganischen Chemie" by Hollemann-Wiberg, 81–90 Edition, Berlin New York, 1976.

Mixtures of various salt hydrates may be employed but only one type of salt hydrate may be used.

There is no upper limit to the amount of salt hydrates which may be employed in accordance with this invention. Only economic considerations limit the amount of salt hydrates which may be employed.

In the process of this invention, the hydrolysis of the Si-bonded alkoxy groups is of course caused not only by the water of hydration contained in the salt and/or liberated during heating, but also by the water formed during the condensation of Si-bonded hydroxyl groups which have been generated through the hydrolysis of Si-bonded alkoxy groups.

By ascertaining the amount of alcohol which has been distilled off, it is possible to control the extent of the hydrolysis of the alkoxy groups, thereby making it possible to control the molecular weight of the polysiloxanes thus formed.

It is preferred that the process of this invention be carried out at atmospheric pressure, i.e., at 1000 millibar or at approximately 1000 millibar. However, if desired, higher or lower pressures may be employed.

The process may be carried out batch-wise, continuously or semi-continuously.

Materials other than those described above may also be employed in the process of this invention. Examples of such additional materials are organic solvents, such as toluene, xylene, cyclohexanone and/or organosiloxanols.

The salt or its partially dehydrated derivative can be separated by simple filtration or by extraction with water.

The organopolysiloxanes prepared in accordance with this invention may be employed in all applications where organopolysiloxanes have been used heretofore. For example the organopolysiloxanes may be used in the preparation of heat resistant and weather-resistant varnishes, as binding agents for mica and glass fabrics, as soaking and impregnation resins and as components of separative coatings.

In addition, the process of this invention may also be used to remove residual alkoxy groups from diorganopolysiloxanes which have been obtained by reacting diorganodichlorosilanes such as dimethyldichlorosilane with alcohols, such as methanol.

In the following examples all parts and percentages are by weight unless otherwise specified.

EXAMPLE 1

A mixture containing 650 grams of an organopolysiloxane consisting of 33 mol percent of dimethylsiloxane units and 67 mol percent of monophenylsiloxane units with 14 percent by weight of Si-bonded methoxy groups and 8 percent by weight of Si-bonded n-butoxy groups and having a viscosity of 140 cs at 25° C. and 65 grams of sodium carbonate-decahydrate, is heated to 90° C. under constant stirring, while methanol is being distilled off. After 70 milliliters of methanol have been distilled off, the reactive mixture is diluted with 162 grams of xylene. After an additional 42 milliliters of methanol have been distilled off, the reactive mixture is cooled to room temperature, and diluted with xylene to an organopolysiloxane content of 50 percent by weight, based on the total weight of the organopolysiloxane and the solvent, and then filtered. The viscosity of the solution obtained is 165 cs at 25° C.

EXAMPLE 2

A mixture containing 650 grams of an organopolysiloxane consisting of 62 mol percent of dimethylsiloxane units and 38 mol percent of monophenylsiloxane units with 19 percent by weight of Si-bonded methoxy groups and a viscosity of 15 cs at 25° C. and 65 grams of sodium carbonate-decahydrate is heated to 90° C. under constant stirring while the methanol is being distilled off. After 107 milliliters of methanol have been distilled off, the reactive mixture is cooled to room temperature, diluted with a mixture containing equal parts by weight of xylene and cyclohexanone until an organopolysiloxane content of 60 percent by weight, based on the total weight of the organopolysiloxane and solvent, is obtained and then filtered. The viscosity of the solution obtained is 320 cs at 25° C.

EXAMPLE 3

A mixture containing 480 milliliters of phenyltriethoxysilane, 198 milliliters of methyltriethoxysilane and 160 grams of sodium carbonate-decahydrate is heated to 90° C. under constant stirring, while ethanol is being distilled off. After 360 milliliters of distillate have been obtained, a sample of the organopolysiloxane contains 48 mol percent of Si-bonded ethoxy groups. After a total of 459 milliliters of distillate has been obtained, the filtered organopolysiloxane still contains 5 mol percent of Si-bonded ethoxy groups.

EXAMPLE 4

About 450 grams of the identical organopolysiloxane used in Example 1 are mixed with 150 grams of an organopolysiloxane consisting of phenylmethylsiloxane units having an Si-bonded hydroxyl group in each of its terminal units and which has a viscosity of 800 cs at 25° C. The mixture thus obtained has a viscosity of 119 cs at 25° C. and when mixed with xylene as a 50 percent solution has a viscosity of 2.6 cs at 25° C. This mixture is mixed with 60 grams of sodium carbonate-decahydrate and heated to 90° C. under constant stirring while methanol is being distilled off. After 40 milliliters of methanol have been distilled off, the reaction mixture is cooled to room temperature, diluted with xylene to an organopolysiloxane content of 50 percent by weight of organopolysiloxane, based on the total weight of solvent and organopolysiloxane, and filtered.

The solution thus obtained, which has a viscosity of 50 cs at 25° C. is used to coat a piece of sheet metal and thereafter the coated metal is heated for 2 hours to 200° C. A hard, elastic, homogeneous film is obtained.

EXAMPLE 5

A mixture consisting of 300 grams of the identical organopolysiloxane used in Example 1 and 30 grams of the salt hydrates listed in the following table is heated to 90° C. under constant stirring while methanol is being distilled off. The following table shows the amounts of methanol and the residual quantities of methoxy groups present in the organopolysiloxane.

| Salt hydrate | Heating Period/hrs. | Methanol ml | Residual methoxy groups, wt.% |
|---|---|---|---|
| $Al_2(SO_4)_3 \cdot 18\ H_2O$ | 6 | 28 | 6.7 |
| $Na_2HPO_4 \cdot 12\ H_2O$ | 7 | 19 | 9.0 |
| $NH_4Fe(SO_4)_2 \cdot 12\ H_2O$ | 8 | 46 | 2.6 |

What is claimed is:

1. A process for increasing the molecular weight of silicon compounds containing Si-bonded alkoxy groups which comprises hydrolyzing silicon compounds containing the Si-bonded alkoxy groups as essentially the only hydrolyzable groups at increased temperature in the presence of a hydrated salt selected from the group consisting of a salt of ammonium hydroxide and a metal of the first to the third principal group of the Periodic System of elements according to Mendeleeff, in an amount of at least 8 grams of hydrated salt per mol of hydrolyzable group while distilling off the alcohol as it is evolved to form a product which does not solidify when cooled to at least room temperature.

2. The process of claim 1, wherein the hydrated salt is sodium carbonate-decahydrate.